United States Patent [19]

Atkinson et al.

[11] Patent Number: 5,762,937
[45] Date of Patent: Jun. 9, 1998

[54] METHODS AND COMPOSITIONS FOR THE EARLY DETECTION AND TREATMENT OF INSULIN DEPENDENT DIABETES MELLITUS

[75] Inventors: Mark A. Atkinson, Gainesville; Noel K. Maclaren, Archer, both of Fla.

[73] Assignee: University of Florida Research Foundation, Inc., Gainesville, Fla.

[21] Appl. No.: 219,816

[22] Filed: Mar. 28, 1994

Related U.S. Application Data

[63] Continuation of Ser. No. 93,821, Jul. 19, 1993, abandoned, which is a continuation of Ser. No. 7,406, Jan. 22, 1993, abandoned, which is a continuation of Ser. No. 569,324, Aug. 17, 1990, abandoned, which is a continuation-in-part of Ser. No. 427,051, Oct. 25, 1989, which is a continuation-in-part of Ser. No. 283,633, Dec. 12, 1988, abandoned.

[51] Int. Cl.$^6$ ............... A61K 35/39; A61K 39/00
[52] U.S. Cl. ............ 424/198.1; 424/94.1; 424/185.1; 424/562; 435/69.3; 530/350
[58] Field of Search ............... 424/184.1, 193.1, 424/185.1, 198.1, 94.1, 562; 530/350, 395, 868, 403; 514/28; 435/69.3

[56] References Cited

U.S. PATENT DOCUMENTS

| | | | |
|---|---|---|---|
| 5,114,844 | 5/1992 | Cohen, et al. | 435/7.21 |
| 5,512,447 | 4/1996 | Baekkeskov et al. | 435/7.4 |
| 5,691,448 | 11/1997 | Baekkeskov et al. | 530/350 |

FOREIGN PATENT DOCUMENTS

| | | | |
|---|---|---|---|
| WO 8906968 | 2/1988 | WIPO | A61K 37/00 |
| WO 9007117 | 12/1989 | WIPO | G01N 33/564 |

OTHER PUBLICATIONS

Bottazo, G.F., R. Lendrum (1976) "Separate autoantibodies to human pancreatic glucagon and somatostatin cells," The Lancet October 23:873–876.

Gorsuch, A.N., K.M. Spencer, J. Lister, E. Wolf, G.F. Bottazzo, A.G. Cudworth (1982) "Can Future Type 1 Diabetes Be Predicted? A Study in Families of Affected Children," Diabetes 31:862–866.

Winter, W.E., N.K. Maclaren, W.J. Riley, R.J. Unger, M. Neufeld, P.T. Ozand (1984) "Pancreatic Alpha Cell Autoantibodies and Glucagon Response to Arginine," Diabetes 33:435–437.

Fundenberg, H. H. et al. (eds), Basic and Clinical Immunology, 34rd edition, chapter 17, pp 207–219, 1980.

Atkinson, M.A., N.K. Maclaren, W.J. Riley, W.E. Winter, D.D. Fisk, R.P. Spillar (1986) "Are Insulin Autoantibodies Markers for Insulin–Dependent Diabetes Mellitus?" Diabetes 35:894–898.

Jewler, D. (1989) "diabetes and the Immune System. Understanding the body's immune system may one day help scientists prevent type 1 diabetes," Diabetes Forecast Aug.:32–40.

Palmer, J.P., D.K. McCulloch (1991) "Perspectives in Diabetes: Prediction and Prevention of IDDM—1991," Diabetes 40:943–947.

Dosa, L. (1988) "Test Helps Predict Childhood Diabetes," Washington Post Health Jun. 21:5.

"Researchers develop juvenile diabetes test," Key West Citizen Jun. 16, 1988.

Beil, L. (1988) "Diabetes antibody best marker so far," Science News Jun. 18, 1988.

"Indicator of IDDM identified," From the American Diabetes Association Scientific Sessions, Jun. 11–14, Medical Week Jun. 20, 1988:2.

Elias, M. (1988) "Diabetes: 'Prevention' is test's goal," USA Today Jun. 15, 1988.

Rusting, R. (1988) "A Better Crystal Ball," Scientific American Aug.:24–25.

Bottazo, G.F., A. Alorin–Christensen, D. Doniach (1974) "Islet–cell antibodies in Diabetes mellitus with autoimmune polyendocrine deficiencies," The Lancet 2:1279–1283.

Palmer, J.P., C.M. Asplin, P. Clemons, K. Lyen, O. Tatpati, P.K. Raghu, T.L. Paquette (1983) "Insulin Antibodies in Insulin–Dependent Diabetics Before Insulin Treatment," Science 222:1337–1339.

Maron, R., D. Elias, B.M. de Johgh, G.J. Bruining, J.J. van Rood, Y. Schechter, I.R. Cohen (1983) "Autoantibodies to the insulin receptor in juvenile onset insulin–dependent diabetes," Nature 303:817–818.

Baekkeskov, S., J.H. Nielsen, B. Marner, T. Bilde, J. Ludvigsson, A. Lernmark (1982) "Autoantibodies in newly diagnosed diabetic children immunoprecipitate human pancreatic islet cellproteins," Nature 298:167–169.

Baekkeskov, M. Landin, J.K. Kristensen, S. Srikanta, G.J. Bruining, T. Mandrup–Poulsen et al. (1987) "Antibodies to a 64,000 M$_r$Human Islet Cell Antigen Precede the Clinical Onset of Insulin–dependent Diabetes," J. Clin. Invest. 79:926–934.

Atkinson, M.A., N.K. Maclaren (1988) "What Causes Diabetes," Scientific American 7:62–67.

Maclaren, N.K. (1988) "Perspectives in Diabetes: How, When, And Why to Predict IDDM," Diabetes 37:1591–1594.

Bottazzo, G.F., R. Lendrum (1976) "Separate autoantibodies to human pancreatic glucagon and somatostatin cells," Lancet 2:873–876.

(List continued on next page.)

*Primary Examiner*—Thomas M. Cunningham
*Attorney, Agent, or Firm*—Saliwanchik, Lloyd & Saliwanchik

[57] ABSTRACT

The invention pertains to the discovery of antigenic cross reactivity between a pancreatic 64K autoantigen and glutamic acid decarboxylase (GAD). Autoantibodies toward GAD were found to be associated with insulin dependent diabetes (IDD). More specifically, the invention pertains to the use of GAD for the diagnosis, prevention and treatment of insulin dependent diabetes (IDD).

2 Claims, 4 Drawing Sheets

OTHER PUBLICATIONS

Atkinson, M.A., N.K. Maclaren (1988) "Autoantibodies in Nonobese Diabetic Mice Immunoprecipitate 64,000-$M_r$ Islet Antigen," Diabetes 33(11):1587–1590.

Baekkeskov, S., H.-J. Aanstoot, S. Christgau, A. Reetz, M. Solimena, M. Cascalho, F. Folli, H. Richter–Oleson, P.-D. Camilli (1990) "Identification of the 64K autoantigen in insulin–dependent diabetes as the GABA–synthesizing enzyme glutamic acid decarboxylase," Nature 347:151–156.

Solimena, M., F. Folli, S. Denis–Donini, G.C. Comi, G. Pozza P. De Camilli, A.M. Vicari 1988) Autoantibodies to glutamic acid decarboxylase in a patient with stiff–man syndrome, epilepsy, and type 1 diabetes mellitus, N.E. J. Med. 318(16):1012–1020.

Atkinson, M.A., N.K. Maclaren, D.W. Scharp, P.E. Lacy, W.J. Riley (1990) "64,000 $M_r$ autoantibodies as predictors of insulin–dependent diabetes," The Lancet 335:1357–1360.

Gerling, I., S. Baekkeskov, A. Lernmark (1986) "Islet cell and 64K autoantibodies are associated with plasma IgG in newly diagnosed insulin–dependent diabetic children," J. Immunol. 137(12):3782–3785.

Geffner, M.E., B.M. Lippe (1987) "The Role of Immunotherapy in Type I Diabetes Mellitus," W. J. Med. 146(3):337–343.

Colman, P.G., U. Di Mario, A. Rabizadeh et al. (1988) "A Prozone Phenomenon Interferes in Islet Cell Antibody Detection: Direct Comparison of Two Methods in Subjects at Risk of Diabetes and in Insulin Dependent Diabetics at Onset," J.Autoimmunity 1:109–117.

Keilacker, H., B. Ziegler, J.M. Diaz–Alonso et al. (1988) "Screening Monoclonal Islet Cell Surface Antibodies (ICSA) by Radioimmunoassay—Detection of Crossreactivity with ICSA from Insulin–Dependent (Type I) Diabetic Patients," Exp. Clin. Endocrinol. 91(1):13–19.

Sakata, S., M. Kobayashi, K. Miura, M.Z. Atassi (1988) "Molecular Recognition of Human Insulin Reception by Autoantibodies in a Human Serum," Immunological Investigations 17(3):237–242.

Solimena, M., F. Folli, R. Aparisi, G. Pozza, P. De Camilli (1990) "Autoantibodies to GABA–ergic neurons and pancreatic beta cells in stiff–man syndrome," N.E. J. Med. 322(22) 1555–1560.

Kobayashi, Y., D.L. Kaufman, A.J. Tobin (1987) "Glutamic Acid Decarboxylase cDNA: Nucleotide Sequence Encoding an Enzymatically Active Fusion Protein," J. Neuroscience 7(9):2758–2772.

Gorsuch, A.N., K.M. Spencer, J. Lister, E. Wolf, G.F. Bottazzo, A.G. Cudworth (1982) "Can Future Type I Diabetes be Predicted? A Study in Families of Affected Children," Diabetes 31:862–866.

Maron, R., D. Elias, B.M. de Jongh, G.J. Bruining, J.J. van Rood, Y. Schechter, I.R. Cohen (1983) "Autoantibodies to the insulin receptor in juvenile onset insulin–dependent diabetes," Nature 303:817–818.

Fundamental Immunology, 1980, Stites (ed.) pp. 226–227, 654–656. Lange Med. Publications.

Galanopoulos, E. et al., Neurochemical Res. 13:243–248, "Effects of fasting and diabetes on some enzymes and transport of glutamate in cortex slices or synaptosomes from rat brain", Mar. 1988.

```
                    .         .       30         .         .       60
         GAAUUCCGCGCAGAAGAGGCGCGGGACGCGCCGGCUUACUGUCGCCUAGCCCAGCCUGUU
           E  F  R  A  E  E  A  R  D  A  P  A  Y  C  R  L  A  Q  P  V

.         .       90         .         .      120
         CCUGCGCGACUGGCCGAGGACCCCGGACAGCAGAGGCCCCAGGACGACCGAGCUGAUG
          P  A  R  D  W  P  R  T  P  D  S  R  G  P  R  T  T  E  L  M

.         .      150         .         .      180
         GCGUCUUCGACCCCUUCUUCGUCCGCAACCUCCUCGAAUGCGGGAGCGGACCCCAAUACU
          A  S  S  T  P  S  S  S  A  T  S  S  N  A  G  A  D  P  N  T

.         .      210         .         .      240
         ACCAACCUGCGCCCCACAACAUAUGACACCUGGUGCGGCGUGGCCCAUGGAUGCACCAGA
           T  N  L  R  P  T  T  Y  D  T  W  C  G  V  A  H  G  C  T  R

.         .      270         .         .      300
         AAACUGGGGCUCAAGAUCUGCGGCUUCCUGCAAAGGACCAACAGCCUGGAAGAGAAGAGC
           K  L  G  L  K  I  C  G  F  L  Q  R  T  N  S  L  E  E  K  S

.         .      330         .         .      360
         CGGCUUGUGAGCGCCUUCAAGGAGAGGCAGUCCUCCAAAAACCUGCUUUCCUGUGAAAAC
           R  L  V  S  A  F  K  E  R  Q  S  S  K  N  L  L  S  C  E  N

.         .      390         .         .      420
         AGCGACAGGGAUGGACGCUUCCGGCGCACGGAGACGGACUUCUCCAACCUGUUUGCUCGA
           S  D  R  D  G  R  F  R  R  T  E  T  D  F  S  N  L  F  A  R

.         .      450         .         .      480
         GAUCUGCUUCCGGCUAAGAACGGGGAAGAGCAAACUGUGCAGUUCCUACUGGAGGUGGUA
           D  L  L  P  A  K  N  G  E  E  Q  T  V  Q  F  L  L  E  V  V

.         .      510         .         .      540
         GACAUACUCCUCAACUAUGUCCGCAAGACAUUUGAUCGCUCCACCAAGGUGCUGGACUUC
           D  I  L  L  N  Y  V  R  K  T  F  D  R  S  T  K  V  L  D  F
```

FIG. 1A

```
                    .          .  570              .          .  600
      CAUCACCCACACCAGCUGCUGGAAGGCAUGGAGGGCUUCAACUUGGAGCUCUCUGACCAC
        H  H  P  H  Q  L  L  E  G  M  E  G  F  N  L  E  L  S  D  H

.          .  630              .          .  660
      CCUGAGUCCCUGGAACAGAUCUUGGUUGACUGCAGAGACACCCUGAAGUAUGGGGUUCGU
        P  E  S  L  E  Q  I  L  V  D  C  R  D  T  L  K  Y  G  V  R

.          .  690              .          .  720
      ACAGGUCACCCUCGAUUUUUCAACCAGCUCUCCACUGGACUGGAUAUCAUUGGUUUAGCU
        T  G  H  P  R  F  F  N  Q  L  S  T  G  L  D  I  I  G  L  A

.          .  750              .          .  780
      GGCGAAUGGCUGACAUCAACUGCCAAUACCAAUAUGUUUACAUAUGAAAUUGCACCAGUA
        G  E  W  L  T  S  T  A  N  T  N  M  F  T  Y  E  I  A  P  V

.          .  810              .          .  840
      UUUGUCCUCAUGGAGCAAAUAACACUUAAGAAGAUGAGGGAGAUAGUUGGAUGGUCAAGU
        F  V  L  M  E  Q  I  T  L  K  K  M  R  E  I  V  G  W  S  S

.          .  870              .          .  900
      AAAGACGGUGAUGGGAUAUUUUCUCCUGGGGGAGCCAUCUCUAACAUGUACAGCAUCAUG
        K  D  G  D  G  I  F  S  P  G  G  A  I  S  N  M  Y  S  I  M

.          .  930              .          .  960
      GCCGCUCGCUACAAGUUCUUCCCGGAAGUUAAGACAAAGGGCAUGGCAGCUGUUCCCAAA
        A  A  R  Y  K  F  F  P  E  V  K  T  K  G  M  A  A  V  P  K

.          .  990              .          . 1020
      CUGGUCCUCUUCACGUCAGAACAUAGUCACUAUUCCAUAAAGAAGGCUGGAGCUGCACUU
        L  V  L  F  T  S  E  H  S  H  Y  S  I  K  K  A  G  A  A  L

.          . 1050              .          . 1080
      GGCUUUGGAACCGACAAUGUGAUUUUGAUAAAGUGCAAUGAAAGGGGGAAGAUAAUUCCA
        G  F  G  T  D  N  V  I  L  I  K  C  N  E  R  G  K  I  I  P
```

FIG. 1B

```
                         1110                      1140
GCUGAUUUAGAGGCAAAAAUUCUUGAAGCCAAGCAAAAGGGAUACGUUCCCCUUUAUGUC
 A  D  L  E  A  K  I  L  E  A  K  Q  K  G  Y  V  P  L  Y  V 1170                      1200
AAUGCAACUGCUGGUACAACUGUUUAUGGAGCUUUCGAUCCCAUACAGGAGAUUGCAGAU
 N  A  T  A  G  T  T  V  Y  G  A  F  D  P  I  Q  E  I  A  D 1230                      1260
AUAUGUGAGAAAUACAACCUGUGGCUACAUGUCGACGCUGCCUGGGGCGGUGGGCUGCUU
 I  C  E  K  Y  N  L  W  L  H  V  D  A  A  W  G  G  L  L 1290                      1320
AUGUCCAGGAAGCACCGCCACAAACUCAGUGGCAUAGAAAGGGCCAACUCAGUCACCUGG
 M  S  R  K  H  R  H  K  L  S  G  I  E  R  A  N  S  V  T  W 1350                      1380
AACCCUCACAAGAUGAUGGGCGUGCUGUUGCAGUGCUCGGCCAUCCUCGUCAAGGAAAAG
 N  P  H  K  M  M  G  V  L  L  Q  C  S  A  I  L  V  K  E  K 1410                      1440
GGUAUACUCCAAGGAUGCAACCAGAUGUGUGCAGGAUACCUUUUCCAGCCAGACAAACAG
 G  I  L  Q  G  C  N  Q  M  C  A  G  Y  L  F  Q  P  D  K  Q 1470                      1500
UAUGAUGUCUCCUAUGACACUGGGGACAAGGCAAUCCAGUGUGGCCGCCACGUGGACAUU
 Y  D  V  S  Y  D  T  G  D  K  A  I  Q  C  G  R  H  V  D  I 1530                      1560
UUCAAGUUCUGGCUGAUGUGGAAAGCAAAGGGCACAGUGGGAUUUGAAAAUCAGAUCAAC
 F  K  F  W  L  M  W  K  A  K  G  T  V  G  F  E  N  Q  I  N 1590                      1620
AAAUGCUUGGAGCUGGCUGAAUACCUCUAUGCCAAGAUUAAAAACAGAGAAGAAUUUGAG
 K  C  L  E  L  A  E  Y  L  Y  A  K  I  K  N  R  E  E  F  E
```

FIG. 1C

```
                .                  .               1650                .                  .               1680
     AUGGUUUUCGAUGGUGAGCCUGAGCAUACAAAUGUCUGUUUCUGGUAUAUUCCACAAAGC
      M   V   F   D   G   E   P   E   H   T   N   V   C   F   W   Y   I   P   Q   S

.                  .               1710                .                  .               1740
     CUCAGGGGCAUUCCAGAUAGCCCUGAACGACGGGAAAAACUACACAGGGUGGCCCCCAAA
      L   R   G   I   P   D   S   P   E   R   R   E   K   L   H   R   V   A   P   K

.                  .               1770                .                  .               1800
     AUCAAAGCCCUGAUGAUGGAGUCUGGCACGACCAUGGUUGGCUACCAGCCCAGGGGGACA
      I   K   A   L   M   M   E   S   G   T   T   M   V   G   Y   Q   P   R   G   T

.                  .               1830                .                  .               1860
     AGGCCAACUUUUUCCGGAUGGUCAUCUCGAACCCAGCUGCUACACAGUCCGAUAUUGACU
      R   P   T   F   S   G   W   S   S   R   T   Q   L   L   H   S   P   I   L   T

.                  .               1890                .                  .               1920
     UCCUCAUCGAGGAGAUAGAAAGACUGGGCCAGGAUCUGUAAUUGCCCUCCAUAGAACAUG
      S   S   S   R   R

.                  .               1950                .                  .               1980
     AGUUUAUGGGAAUCCCCUUUCCUUCUGGCAUUCUAGAAUAACCUCUAUAAAUUGCCAAAA

.                  .               2010                .                  .               2040
     CACAUAGGCUAUUUCACUGAGGGAAAAUAUAAUAUCUUGAAGACUACUGUUUAAACAUUA

.                  .               2070                .                  .               2100
     CUUAAGCUUGUUCUAGUAUGUAGGAAAUAAUGUUCUUUUUAAAAAGUUGCACAUUAGGAA

.                  .               2130                .                  .               2160
     CACAGUAUAUAUGUACAGUUAUAUAUACCUCUCUCUGUAUAUGUAUAUGUAUGUAUAGUG

.                  .               2190                .                  .               2220
     AGUGUGGCUUGGUGAUAGAUCACAGCAUGUGUCCCCCUCCAAGAGAAUUAACUUUACCUU

.                  .               2250                .
     CAGCAGCUACUGAGGGGCCAAACAUGCUGCAAACCUGCGGAAUUC
```

FIG. 1D

METHODS AND COMPOSITIONS FOR THE EARLY DETECTION AND TREATMENT OF INSULIN DEPENDENT DIABETES MELLITUS

CROSS REFERENCE TO RELATED APPLICATIONS

This application is a continuation of U.S. patent application Ser. No. 08/093,821, filed Jul. 19, 1993, now abandoned; which is a continuation of application Ser. No. 08/007,406, filed Jan. 22, 1993, now abandoned; which is a continuation of application Ser. No. 07/569,324, filed Aug. 17, 1990, now abandoned; which is a continuation in part of application Ser. No. 07/427,051, filed Oct. 25, 1989; which is a continuation in part of application Ser. No. 07/283,633, filed Dec. 12, 1988, now abandoned.

This invention was made with government support under NIH Grant Nos. PO1DK39079 and RO1HD19469. The government has certain rights in this invention.

BACKGROUND OF THE INVENTION

Diabetes is a major public health problem. As reported by the 1987 report of The National Long-Range Plan to Combat Diabetes of the National Diabetes Advisory Board, six million persons in the United States are known to have diabetes, and an additional 5 million have the disease which has not yet been diagnosed; each year, more than 500,000 new cases of diabetes are identified. In 1984, diabetes was directly causal in 35,000 American deaths and was a contributing factor in another 95,000.

Ocular complications of diabetes are the leading cause of new cases of legal blindness in people ages 20 to 74 in the United States. The risk for lower extremity amputation is 15 times greater in individuals with diabetes than in individuals without it. Estimates suggest that persons with diabetes undergo over one-half of the approximately 125,000 amputations performed annually in the United States.

Kidney disease is a frequent and serious complication of diabetes. Approximately 30 percent of all new patients in the United States being treated for end-stage renal disease have diabetes. This percentage is increasing at a rate of approximately 2 percent annually; therefore, within the next decade, diabetes-related kidney disease will account for more than one-half of all enrollees in the End-Stage Renal Disease Program.

Individuals with diabetes are also at increased risk for periodontal disease. Periodontal infections advance rapidly and lead not only to loss of teeth but also to compromised metabolic control. Women with diabetes risk serious complications of pregnancy. Current statistics suggest that the mortality rates of infants of mothers with diabetes is approximately 7 percent.

The economic burden of diabetes is enormous. Each year, patients with diabetes or its complications spend 24 million patient-days in hospitals. A conservative estimate of total annual costs attributable to diabetes is at least $24 billion (American Diabetes Association est., 1988); the full economic impact of this disease is even greater because additional medical expenses often are attributed to the specific complications of diabetes rather than to diabetes itself.

Diabetes is a chronic, complex metabolic disease that results in the inability of the body to properly maintain and use carbohydrates, fats, and proteins. It results from the interaction of various hereditary and environmental factors and is characterized by high blood glucose levels caused by a deficiency in insulin production or an impairment of its utilization. Most cases of diabetes fall into two clinical types: insulin-dependent diabetes mellitus (IDDM or IDD) and non-insulin-dependent diabetes mellitus (NIDDM or NIDD). Each type has a different prognosis, treatment, and cause.

Approximately 5 to 10 percent of diabetes patients have IDD, formerly known as juvenile diabetes because of its frequent appearance early in life, usually in childhood or adolescence. IDD is characterized by a partial or complete inability to produce insulin. Patients with IDD would die without daily insulin injections to control their disease.

Few advancements in resolving the pathogenesis of diabetes were made until the mid-1970s when evidence began to accumulate to suggest that IDD had an autoimmune etiopathogenesis. It is now generally accepted that IDD results from the chronic autoimmune destruction of the insulin producing pancreatic β-cells. Lymphocytes and other inflammatory cells have been observed within the islets of Langerhans in newly diagnosed IDD patients and have been found preferentially in regenerating islets composed of β-cells rather than those of other cell types. This active immunological process is associated with a variety of autoantibodies to β-cell cytoplasmic and membrane antigens, insulin, and insulin receptors.

Thus, IDD is a disease which is replete with autoantibodies. These include islet cell autoantibodies of the cytoplasmic type (ICA) (Bottazzo, G. F., A. Florin-Christensen, and D. Doniach [1974] Lance. 2:1279–1283); islet cell surface autoantibodies (ICSA) (Maclaren, N., S. W. Huang, and J. Føgh [1975] Lancet. i:997–1000); insulin autoantibodies (IAA) (Palmer, J. P., C. M. Asplin, and P. Clemons [1983] Science 222:1337–1339) and the possible antiidiotypic insulin receptor autoantibodies (Ins.R.A.) (Maron, R., D. Elias, M. de J. Bartelt, G. J. Bruining, J. J. Van Rood, Y. Shechter, and I. R. Cohen [1983] Nature 303:817–818). In 1982 it was reported that antibodies to a 64,000 $M_r$ islet cell antigen were detected in IDD patients (Bækkeskov, S. et al. [1982] Nature 298:167–169). In a subsequent publication, Bækkeskov et al. reported the 64,000 $M_r$ antibodies associated with the IDD in the BB rat model (Bækkeskov, S. et al. [1984] Science 224:1348–1350). Later, a follow-up study investigated patients who were related to individuals with IDD and, thus, were known to be at risk for developing the disease (Bækkeskov, S. et al. [1987] J. Clin. Invest. 79:926–934). The results of this later study suggested that the 64,000 $M_r$ antibodies may be present in some IDD patients before the manifestation of clinical symptoms. However, in that same study, Bækkeskov et al. reported that the function of the 64,000 $M_r$ protein was unknown and that the data was inconclusive as to whether or not 64,000 $M_r$ antibodies were present before a decrease in β-cell function commenced.

Other antibodies to various non-β-cell specific molecules have been reported with an increased prevalence in IDD patients. These include antibodies to tubulin, single stranded and double stranded DNA, gastric parietal cells, intrinsic factor adrenocortical cells, thyroid peroxidase enzymes, and thyroglobulin. IDD patients have signs of polyclonal activation of B-lymphocytes, and the increased antibody titers to various antigens may be the result.

Furthermore, studies during the past decade have shown that patients with IDD have genetic markers, called histocompatibility antigens, that are associated with susceptibility to IDD. Because these genetic susceptibility markers are necessary but not sufficient for the development of IDD, it appears that some additional, as yet unknown, environmental factors could be required to initiate the destruction of the β-cells and the development of diabetes. Environmental factors, either viruses or chemical agents, may initiate an immune response against the β-cells to permit their immunologic destruction in genetically susceptible individuals (Atkinson, M. A., and N. K Maclaren. [1990] Scientific American 7:62–67). Therefore, identification of the prediabetic state in diabetes is essential in efforts to prevent the development of the disease. Perhaps the single most important advance of the past two decades in diabetes research has been recognition that autoimmune destruction of β-cells takes months or years to reach completion. Whereas currently the clinical diagnosis of diabetes is almost never made until the destructive process is nearly complete and insulin injections are required to prevent death, intervention before the insulin-producing cells have been irreversibly destroyed can provide a strategy to prevent progression of diabetes and its complications.

It is crucial, therefore, to find a means of accurately predicting the onset of IDD before the disease has progressed to the clinical stage.

Although many biological markers have been associated with IDD, until now, none of these markers have been shown to be uniformly present before the onset of the clinical symptoms of the disease (Maclaren, N. K. [1988] Diabetes 37:1591–1594). Such early presence is essential for a compound to qualify as a useful predictive test for the disease. However, early presence alone is not sufficient for an accurate early detection method; a predictive test based on the presence or absence of a particular marker is valuable only if the predictive marker is present only in those who will get IDD, and not present in those who will not. Because the treatments for diabetes, as well as the psychological impacts of the disease, can have a profound effect on the health of the diagnosed individual, it is crucial to develop a predictive test which is specific and, thus, provides very few false positives.

It is also crucial to identify a predictive test which can recognize the onset of the disease years before the clinical symptoms appear. This early detection provides an opportunity for treatments which can forestall or prevent the serious health problems associated with the clinical stages of IDD. For example, nonspecific immunosuppression trials with drugs such as Cyclosporin A, azathioprine and steroids have been undertaken in newly diagnosed patients. Over the first year of their use, a limited number of remissions have been obtained, but these patients are never restored to normal since pancreatic β-cells have only limited regenerative capacity, and treatments begun at the time of diagnosis are most often too late.

Until now, no suitable predictive test for IDD meeting these requirements has been found. Although many autoantibodies have been associated with the disease, research into identifying uniformly predictive autoantibodies has not been successful. For example, as early as 1976, autoantibodies have been described which reacted with the cytoplasm of the glucagon-secreting (alpha) cells (ACA) of the islet (Bottazzo, G. F., and R. Lendrum [1976] Lancet 2:873–876). Because autoantibodies against endocrine glands are sometimes found to precede or accompany the clinical onset of disease, it was thought that ACA could be a predictive marker for deficiency of the islet hormone, glucagon. Unfortunately, subsequent research revealed that ACA did not appear to be associated with defective alpha cell function, with IDD, or with any identifiable pancreatic pathology (Winter, W. E., N. K. Maclaren, W. J. Riley, R. H. Unger, M. Neufeld, and P. T. Ozand [1984] Diabetes 33(5):435–437).

Research into the predictive value of other antibodies associated with the pancreas and the clinical stages of IDD have produced a means for early detection of the disease. For example, both insulin autoantibodies (IAA) and islet cell autoantibodies (ICA) have been found to be present in many newly diagnosed patients. The ICA have been shown to be present in advance of the clinical stages of IDD, specifically in non-diabetic relatives at risk for IDD. However, neither ICA or IAA provide a predictive test with near absolute specificity and sensitivity for IDD.

Therefore, there exists a substantial and long-felt need for a more accurate means of detecting IDD in its early stages prior to the onset of clinical symptoms and the requirement of insulin therapy.

BRIEF SUMMARY OF THE INVENTION

The invention described here concerns a novel means of accurately detecting the early stages of Insulin Dependent Diabetes Mellitus (IDD). Specifically, IDD can be detected before a significant loss of β-cell function. Also described are means of treating IDD in its initial stages.

In particular, it has been found that autoantibodies to an islet cell 64,000 $M_r$ protein, are present up to several years before the clinical manifestations of IDD are observed. The antibodies have been designated 64KA. The early detection of this potentially devastating disease would facilitate the administration of intervention treatments which would not be effective during the later stages of the disease when irreversible damage is extensive.

The 64KA can be used alone, or in combination with other autoantibodies such as ICA and IAA which are known to be associated with IDD, to detect and predict the onset of IDD. The 64KA described here are highly disease specific for IDD. The 64KA have been found to be present uniformly in children and young adults studied months to years prior to their onset of IDD. The 64KA test was found to predict the onset of IDD when other antibodies associated with the disease could not.

The protein antigens reactive with the 64KA are also revealed to be useful in the treatment of IDD. Described here as part of the subject invention are novel means for halting or slowing the onset of IDD. The novel means of treatment involves the construction of novel hybrid β-cell 64K proteins—toxin products which are capable of disabling immunological mediators involved in the pathogenesis of IDD.

A further aspect of the invention is the use of 64KA to diagnose and prevent impending destruction of pancreas islet cell transplants by minimizing immune-related destruction and rejection of the new pancreas by administration of the 64K hybrid toxin molecules. Additionally, the invention concerns the use of anti-idiotypic antibodies to the 64KA as a means of intervention therapy.

The subject invention further concerns the discovery that the pancreatic 64K protein has sequence homology with a glutamic acid decarboxylase (GAD) protein. Furthermore, the 64K protein has immunologic reactivity with antibodies to the GAD enzyme. Therefore, a further element of the subject invention pertains to the use of a GAD protein, or immunologically active fragments thereof, for the diagnosis, prevention, and treatment of IDD.

BRIEF DESCRIPTION OF THE DRAWING

FIG. 1 shows nucleotide and derived amino acid sequence of the feline glutamic acid decarboxylase mRNA.

DETAILED DESCRIPTION OF THE INVENTION

The invention described here relates to the use of a 64K autoantibody as an accurate and specific early indicator of the onset of IDD. The identification of 64KA as a useful predictive marker for IDD resulted from exhaustive biochemical research focusing on a multitude of compounds associated with IDD. The high specificity of 64KA for IDD, as well as the frequent presence of 64KA in individuals years before the onset of IDD, were both unexpected. These attributes of 64KA make it useful as a means of early detection of IDD.

In order to ascertain whether specific entities are valid predictors of the onset of IDD, it is necessary to determine whether these entities are present before clinical symptoms of diabetes occur. This prediabetic period has been difficult to study because large numbers of high risk relatives of affected probands must be screened for circulating autoantibodies to identify the susceptible individuals, and long periods of observations are necessary to document the natural history of the β-cell failure in the disease. Therefore, animal models have been used to augment and further confirm data obtained for human tests.

The non-obese diabetic (NOD) mouse is a useful animal model for human IDD. Analysis of the NOD mouse provides important insights into the sequence of pathogenic events and leads to an understanding of the nature of the target islet cell autoantigens involved in the autoimmunological process. Another important model for IDD is the Biobreeding (BB) rat. The subject invention was discovered as a result of research and studies involving humans, BB rats, and NOD mice.

It was found that in IDD of man and the BB rat model, islet cell autoimmunities are associated with autoantibodies to a β-cell protein of relative molecular mass ($M_r$) 64,000 (64K). It has also been determined that sera from newly-diagnosed NOD mice similarly contain an autoantibody that immunoprecipitates the 64K antigen from detergent lysates of $^{35}$S methionine labelled murine islet cells (Atkinson, M., and N. K. Maclaren [1988] Diabetes 38:1587–1590). In NOD mice, the autoantibody was detectable by the time of weaning, it disappeared within weeks after diabetes onset, and was absent in older non-diabetic mice as well as all of three non-diabetes-prone control strains tested.

In humans, the 64KA were present before clinical diagnosis in 96% of individuals who subsequently were under the age of 35 at IDD onset. The 64KA were found to be predictably present well in advance of the clinical manifestations of IDD. Also, the presence of 64KA was found to be highly specific to IDD; unlike IAA or ICA, 64KA has not been observed in individuals who are not at high risk, or increased risk, to develop IDD.

Materials and Methods

Islet Cell Preparations

Human pancreatic islets were isolated from cadaveric pancreases as previously reported (Diabetes 37:413–420, 1988). All batches of islets were maintained in vitro in supplemented media CMRL 1066. A mean of 84,946±11, 061 (x±SEM, n=12) isolated human islets per batch were obtained with a mean islet purity of 91.2±2.3%, and an insulin content of 0.4±0.1 mU insulin per islet. Perfusion testing of KREBS with alternating glucose concentrations of 60 mg/dl–300 mg/dl gave a mean insulin stimulation index of 4.68±0.66 (G300/G60). All batches were labeled within 7 days.

Metabolic Labeling of Islet Cells

Following a minimum of 36 hours of in vitro culture (6000 islets/50 ml RPMI 1640 medium supplemented with 16 mM glucose, 20 mM HEPES, 100 uU/ml penicillin, 100 μg/ml streptomycin, 2% (v/v) normal human serum, 37° C., 95% air/5% $CO_2$), the islets were reseeded and incubated for 15 minutes in supplemented RPMI 1640 medium (1000 islets/ml) which was deficient in methionine. The cells were then incubated for 5 hours at 37° C. (95% air/5% $CO_2$) in methionine free medium (1000 islets/ml) to which $^{35}$S methionine (>500 Ci/mmol) had been added at a concentration of 0.5 mCi/1×10$^3$ islet cells. The cells were next incubated with supplemented methionine containing (0.5 mM) RPMI 1640 medium (1000 islets/ml) for 30 minutes, washed twice (200×g, 5 minutes) in buffer containing 20 mM Tris (pH 7.4), 150 mM NaCl, 100 KIE/ml aprotinin, and 2 mM phenylmethyl sulfonyl fluoride (PMSF), and then snap frozen (–80° C.) until their detergent extraction.

Immunoprecipitation of 64K Autoantigen

The islet cells were lysed in the above buffer containing 2% TRITON™ X-114. The insoluble material was removed by ultracentrifugation (100,000×g, 30 minutes, 4° C.). The lysate was then separated into aqueous, sucrose, and detergent phases prior to immunoprecipitation (Bordier, C. [1981] J. Biol. Chem 256:1064–1067). The lysate was incubated with normal control human serum (10 μl per 100 μl supernatant, 1 hour, 4° C.) followed by adsorption to an excess of protein A Sepharose CL-4B (100 μl swollen protein A Sepharose to 25 μl sera). Aliquots (100 μl containing 5–10×10$^6$ cpm) of unbound (pre-cleared) lysate were incubated with 25 μl of test sera (either IDD or control) for 18 hours (4° C.). Detergent extracts from 1000 islets for each serum sample tested was used. To each assay tube, 100 μl of pre-swollen protein A Sepharose CL-4B were added, and the reaction mixture was incubated for 45 minutes (4° C.). The protein A Sepharose CL-4B was then washed five times by centrifugation (200×g, 10 seconds) in 0.5% TRITON™ X-114 buffer and once in ice cold double distilled water (200×g, 30 seconds). Bound proteins were eluted and denatured by boiling for 3 minutes in sample buffer containing 80 mM Tris (pH 6.8), 3.0% (w/v) sodium dodecyl sulfate (SDS), 15% (v/v) sucrose, 0.001% (v/v) bromphenyl blue, and 5.0% (v/v) β-mercaptoethanol. The Sepharose beads were removed by centrifugation (200×g, 1 minute) and the supernatant electrophoresed through discontinuous SDS 10% polyacrylamide separating gels, followed by Coomassie Brilliant Blue staining and fluorography using Enhance (New England Nuclear, Boston, Mass.).

ICA Analysis

ICA were assayed by indirect immunofluorescence on blood group O cryocut pancreatic sections as described in (Neufeld, M. N. Maclaren, W. Riley, D. Lezotte, H. McLaughlin, J. Silverstein, and A. Rosenbloom [1980] Diabetes 29:589–592). All results were read on coded samples, with control negative and positive sera in each batch. Sera were considered positive if immunofluorescence of the tissue was observed within the pancreatic islets. Positive results are those in which the autoantibody exceeds a concentration (or titer) of 10 Juvenile Diabetes Foundation (JDF) units, as defined by the Immunology of Diabetes Workshops (IDW) and standardized by a worldwide ICA proficiency testing program administered by Noel K. Maclaren.

Insulin Autoantibody Binding Procedure

The RIA method used to detect IAA was modified to maximize sensitivity without loss of specificity for IDD. Mean serum insulin binding was calculated from sera obtained from 94 non-diabetic Caucasian children and lab personnel (mean age 13.7±7.7 yrs., 51 males/43 females) lacking a family history of IDD. None of these control individuals were positive for ICA. Optimal results were found using monoiodinated human insulin radiolabeled with $^{125}I$ at the A14 position at a concentration of 0.15 ng/ml. More recently, improved specificity of the assay has been achieved by determination of specific binding which was displaceable through the addition of excess unlabeled insulin.

IVGTT Procedure

In order to investigate the insulin response to glucose stimulation, an intravenous glucose tolerance test (IVGTT) was performed (Srikanta, S., O. P. Ganda, G. S. Eisenbarth, and J. S. Soeldner [1983] N. Engl. J. Med. 308:322–325) with the dose of administered glucose at 0.5 g/Kg given intravenously precisely over 2–4 minutes. Serum samples were collected at −10, 1, 3, 5, 10, 15, 30, and 60 minutes post glucose infusion. Insulin deficiency was defined when the insulin level at 1 minute and 3 minute together were <3rd percentile for a control population of ICA negative non-IDD individuals (n=150, Age 20.3±10.2 years, range 2 to 59 years). For this analysis, insulin values less than 70 μIU/ml (<3rd percentile for the 150 controls) were considered to be insulinopenic.

HLA DR Typing

HLA DR typing was performed as adapted from the method described by Van Rood and Van Leuwen (Van Rood, J. J., A. Van Leuwen, and J. S. Ploem [1976] Nature 262:795–797). Standard reference antisera were used for typing.

Construction of Human Islet cDNA Library

A cDNA library for human islet cells has been constructed in the lambda gt11 vector (Young, R. A., and Davis, R. W. [1983] Proc. Natl. Acad. Sci. USA 80:1194–1198). Messenger RNA was isolated and purified from approximately 200,000 purified human islets according to a modification of the method of Chirgwin et al (Chirgwin, J. M., A. E. Przybyla, R. J. MacDonald, and W. J. Rutter [1979] Biochemistry 18:5294–5299). The islets were lysed in 4M guanidine thiocyanate containing 1M 2-mercaptoethanol and 0.1M Tris-HCl (pH 7.4). The lysate was layered over a 5.7M cushion of CsCl and subjected to centrifugation at 37,000 rpm in a Beckman SW50.1 rotor for 17 hours. The RNA pellet was removed and resuspended in sterile water followed by precipitation with three volumes of absolute ethanol. This final step was repeated three times to insure a clean preparation of RNA The cDNA for the library was synthesized using human islet total RNA as template and the enzyme reverse transcriptase in the presence of human placental ribonuclease inhibitor, oligo(dT) primer, and the four deoxyribonucleotide triphosphates. The mixture was incubated at 40° C. for 2 hours. The second strand of the cDNA was synthesized using the products of the first strand reaction and the enzymes E. coli DNA polymerase I and E. coli ribonuclease H. The mixture was incubated sequentially at 12° C. for 60 min then 22° C. for 60 min followed by heat inactivation at 65° C. for 10 min. To insure that the ends of the cDNA were flush, the mixture was incubated with T4 DNA polymerase for 10 min at 37° C. This mixture of double-stranded cDNA (ds-cDNA) was then purified using extraction with an equal volume of buffer saturated phenol/chloroform, followed by an extraction with an equal volume of chloroform. The unincorporated nucleotides were removed by the addition of an equal volume of 4M ammonium acetate followed by the addition of two volumes of absolute ethanol. After chilling for 15 min on dry ice, the mixture was centrifuged for 10 min at 12,000 rpm in a microcentrifuge. This precipitation step was repeated two times to insure the complete removal of the unincorporated nucleotides.

The ds-cDNA was prepared for cloning into the vector by a series of modification steps, beginning with an incubation with the enzyme EcoRI methylase in the presence of s-adenosyl-methionine for 1 hour at 37° C. This methylated cDNA was ligated to synthetic EcoRI linkers in the presence of T4 DNA ligase and ATP overnight at 15° C. Cohesive EcoRI ends were generated on the linkered cDNA by digestion with EcoRI endonuclease for 5 hours at 37° C. Following this step, the excess linkers were removed from the mixture by column chromatography. The material that eluted in the void volume of this column represented the ds-cDNA that had been methylated, ligated to EcoRI linkers, and size-selected.

This material was ligated to lambda gt11 vector that had been digested with EcoRI and treated with alkaline phosphatase. The ligation proceeded in the presence of T4 DNA ligase and ATP overnight at 15° C. Each ligation mixture was packaged into phage lambda coat proteins using a commercially available extract (Stratagene). The levels of packaged phage were determined by titration on the E. coli host strain, Y1088. The complexity of the library was determined to be approximately $2.0 \times 10^6$ pfu, of which 81% contained inserted cDNA as detected by the absence of color on bromo-chloro-indolyl-galactoside (BCIG) indicator. The recombinant library was amplified prior to screening with ologonuleotide probes.

Following are examples which illustrate procedures, including the best mode, for practicing the invention. These examples should not be construed as limiting. All percentages are by weight and all solvent mixture proportions are by volume unless otherwise noted.

Statistical analysis included both Chi-square analysis after the Yate's correction factor was applied, and Fisher's exact test (Snedecor, T. N. and W. G. Cochran [1967] Statistical Methods. Iowa State University Press, Ames, Iowa).

EXAMPLE 1

Association of 64KA with IDD

Five groups of individuals were selected for the 64KA studies. There were 31 newly diagnosed patients with IDD, defined according to the established National Diabetes Data Group (NDDG) criteria (National Diabetes Data Group [1979] "Classification and Diagnosis of Diabetes Mellitus and Other Categories of Glucose Intolerance," Diabetes 28:1039–1057). Also studied were 26 nondiabetic controls who lacked ICA and any known family history of autoimmune disease; 40 nondiabetic ICA and IAA lacking relatives of the aforementioned newly-diagnosed patients; 36 nondiabetic but ICA positive individuals of whom 28 were first degree relatives of probands with IDD, 4 were apparently healthy normal controls, and 4 were patients with Autoimmune Addison's disease or thyroiditis; 5 ICA negative but high titer IAA positive children who were unaffected relatives of probands with IDD, and 28 additional individuals whose sera had been collected prior to their documented onset of IDD.

The above patients were obtained through two ongoing prospective ICA screening population studies of more than 5000 first degree relatives of IDD probands, and 8200 normal control individuals of which approximately 5000 were school children. All sera were stored at 20° C. from 1 week to 7 years prior to autoantibody analysis.

The 64KA was found to be extremely disease specific in that it was present in 84% of newly diagnosed IDD patients, and was completely absent from the control population tested (p<0.0001).

EXAMPLE 2

64KA as Predictor of IDD

In order to analyze the capacity of 64KA to actually predict the onset of IDD, serum samples from 28 individuals were analyzed for 64KA. The serum samples had been taken prior to the onset of any clinical manifestations of IDD. Each of the 28 individuals developed clinical symptoms of IDD at some later point in their life. Of these 28 individuals, 25 developed clinical symptoms before age 35.

It was found that the 64KA were present in 24 of the 25 (96%) of the individuals who were under age 35 at the onset of clinical IDD. The serum samples tested from these individuals had been taken anywhere from 3 months to 7 years (mean 27 months) prior to the clinical onset of IDD. The presence of 64KA occurred as early as 7 years prior to the onset of clinical symptoms.

The same serum samples were also tested for the presence of ICA and IAA. In contrast to the 64KA which was present in 82% of all cases, ICA was present in 22 out of 28 (78%) samples, and IAA were present in only 13 out of 27 (48%) of the samples. These results are presented in Tables 1 through 4. Clearly, the predictive value of 64KA for IDD was the best of all three autoantibodies.

In a separate analysis of 9 IDD parients after onset of disease, the retention of response SUSTACAL™ versus the loss of islet cell insulin reserve displayed a better correlation with 64KA than ICA. Therefore, 64KA also provides an indication of remaining β-cell mass.

TABLE 1

Frequency of 64,000 Mr Autoantibodies.

| Group | n | 64KA | ICA |
|---|---|---|---|
| Control | 26 | 0(0) | 0(0) |
| Newly Diagnosed IDD | 31 | 26(84) | 25(81) |
| ICA−/IAA− Relative | 40 | 1(2) | 0(0) |
| ICA+ Relative | 28 | 23(82) | 28(100) |
| ICA+ others | 8 | 7(87) | 8(100) |
| ICA−/IAA+ <5 yr age | 5 | 4(80) | 0(0) |

TABLE 2

Summary of the Findings of Non-diabetic Patients at Risk for IDD Because of ICA Positivity

| Sex | Age | HLA-DR | Ascertainment | ICA* | 64K | IAA | Plasma insulin IVGTT (1 + 3 min (% tile) |
|---|---|---|---|---|---|---|---|
| M | 6 | 3,— | IDD family study | 80 | + | − | 144 (40) |
| M | 9 | 3,1 | IDD family study | 40 | + | − | 57 (<1) |
| F | 11 | 3,4 | IDD family study | 80 | + | + | ND |
| M | 11 | 3,4 | IDD family study | 80 | + | + | 105 (20) |
| F | 12 | 4,3 | IDD family study | 40 | + | − | 194 (60) |
| F | 13 | 2,4 | IDD family study | 40 | + | + | 62 (<3) |
| M | 17 | 3,4 | IDD family study | 20 | + | − | 67 (<3) |
| M | 20 | 2,4 | IDD family study | 40 | + | + | 58 (<1) |
| F | 29 | 3,4 | IDD family study | 40 | + | − | 57 (<1) |
| F | 30 | 3,— | IDD family study | 160 | + | − | 82 (10) |
| F | 33 | 3,8 | IDD family study | 20 | + | − | 125 (30) |
| F | 34 | 3,4 | IDD family study | 40 | + | − | 167 (50) |
| M | 44 | 4,1 | IDD family study | 20 | − | − | ND |
| F | 10 | 4,8 | IDD family study | 360 | + | − | 98 (20) |
| F | 38 | 4,— | IDD family study | 20 | + | + | 71 (5) |
| M | 7 | 4,8 | IDD family study | 40 | + | + | 114 (25) |
| M | 7 | 3,4 | IDD family study | 20 | + | + | 116 (25) |
| M | 10 | 4,— | IDD family study | 160 | + | + | 52 (<1) |
| F | 10 | 5,9 | IDD family study | 20 | + | + | 128 (30) |
| F | 43 | 3,1 | IDD family study | 80 | − | − | 293 (70) |
| F | 13 | 1,3 | IDD family study | 80 | − | − | 100 (20) |
| M | 5 | 2,4 | IDD family study | 40 | + | − | 125 (30) |
| F | 39 | 4,— | IDD family study | 80 | + | + | 112 (25) |
| M | 11 | 3,4 | IDD family study | 40 | + | + | 56 (<1) |
| F | 35 | 4,7 | IDD family study | 40 | + | − | 420 (90) |
| M | 43 | 3,7 | IDD family study | 160 | − | − | ND |
| F | 38 | 3,4 | IDD family study | 20 | − | − | 184 (60) |
| F | 26 | ND | IDD family study | 40 | + | + | ND |
| M | 8 | 3,4 | School study | 160 | + | + | 67 (<3) |
| M | 10 | 3,4 | School study | 160 | − | − | 268 (75) |
| F | 13 | 4,6 | School study | 40 | + | − | 67 (<3) |
| M | 11 | 3,4 | School study | 320 | + | + | 124 (30) |
| M | 16 | 3,4 | Addison's/Thyroiditis | 160 | + | − | ND |
| M | 32 | 3,4 | Addison's/Thyroiditis | 80 | + | − | 197 (60) |
| F | 41 | 3,4 | Addison's/Thyroiditis | 320 | + | + | 69 (<3) |
| M | 12 | 3,4 | Addison's/Thyroiditis | 160 | + | − | 149 (40) |

*JDF units

TABLE 3

Summary of Findings of the First Serum Sample Available from Patients Tested Prior to their Development of IDD

| | | | | | IDD Associated | | |
| | | | | Prediabetic | | Autoantibodies | |
| | | Age at | | | | | |
| Sex | HLA-DR | Onset | Ascertainment | Period (mo) | ICA* | 64K | IAA |
|---|---|---|---|---|---|---|---|
| M | 3,3 | 5 | IDD family study | 9 | – | + | – |
| M | 4,6 | 10 | IDD family study | 34 | 20 | + | + |
| F | 4,7 | 11 | IDD family study | 34 | 40 | + | + |
| M | 3,3 | 12 | IDD family study | 8 | 40 | + | – |
| F | 4,6 | 15 | IDD family study | 3 | 80 | + | – |
| M | 3,4 | 15 | IDD family study | 19 | 80 | + | + |
| M | 3,4 | 17 | IDD family study | 14 | – | + | – |
| M | 3,4 | 19 | IDD family study | 3 | 40 | + | – |
| M | ND | 21 | IDD family study | 32 | 80 | + | – |
| F | 4,— | 33 | IDD family study | 14 | 10 | + | + |
| F | 4,5 | 38 | IDD family study | 2 | 80 | – | – |
| M | 3,4 | 42 | IDD family study | 42 | 80 | + | + |
| M | 4,6 | 5 | IDD family study | 30 | –** | –** | + |
| M | 3,4 | 15 | IDD family study | 6 | – | + | + |
| M | 3,4 | 30 | IDD family study | 13 | 160 | + | ND |
| M | ND | 4 | IDD family study | 3 | 20 | – | – |
| M | 6,1 | 33 | IDD family study | 14 | –** | + | – |
| F | 4,6 | 37 | IDD family study | 3 | 80 | – | – |
| F | 3,4 | 7 | gluc intol | 11 | +(NT) | + | + |
| M | 4,4 | 15 | gluc intol | 2 | 80 | + | + |
| F | 3,6 | 17 | gluc intol | 2 | 20 | + | – |
| M | 2,3 | 18 | gluc intol | 12 | 40 | + | – |
| M | ND | 27 | gluc intol | 6 | 40 | + | + |
| F | 2,3 | 40 | gluc intol | 19 | +(NT) | – | – |
| F | 1,4 | 9 | school study | 3 | 40 | + | + |
| F | 3,4 | 12 | school study | 44 | 320 | + | + |
| F | 3,3 | 24 | Graves disease | 72 | –** | + | – |
| F | 1,4 | 14 | Thyroiditis | 75 | +(NT) | + | + |
| | | | | | 22/28 (78%) | 23/28 (82%) | 13/27 (48%) |

NT = Not JDF Titred
ND = Not Determined
* = JDF units
** = Converted to Autoantibody Positivity at a Subsequent Sample Date

TABLE 4

Summary of the Findings of Non-diabetic Patients at Risk for IDD Because of IAA Positivity

| | | | | IDD Associated Autoantibodies | | | Plasma insulin IVGTT |
|---|---|---|---|---|---|---|---|
| Sex | Age | HLA-DR | Ascertainment | ICA | 64K | IAA | (1 + 3 min (% tile) |
| F | 2 | 4,5 | IDD family study | – | + | + | 129 (40) |
| M | 3 | 2,1 | IDD family study | – | + | + | 27 (<1) |
| F | 5 | ND | IDD family study | – | + | + | ND |
| M | 0.5 | 1,6 | IDD family study | – | + | + | 342 |
| F | 3 | ND | IDD family study | – | – | + | ND |

EXAMPLE 3

Association of 64KA with IDD in NOD Mice

Recently, two types of animals (the BB rat and NOD mouse) have been developed that can serve as models for studying human IDD. The use of animal models to evaluate predictors of IDD is very valuable because the pre-diabetic period is difficult to study due to the large numbers of high risk relatives of affected probands which must be screened for circulating autoantibodies in order to identify the susceptible individuals, and because of the long periods of observations which are necessary to document the natural history of β-cell failure in the disease. The NOD mouse and the BB rat provide important insights into the sequence of pathogenic events involved in human IDD. Analysis of these animals can also help lead to an understanding of the nature of the target islet cell autoantigens involved in the autoimmunological process. We therefore studied NOD mice and BB rats for their possible 64K autoantibodies, both prior to and after IDD onset.

Sera were obtained from both male and female NOD and control (BALB/c, C57BL/6, C2H/Hej) strains of mice of various ages. Diagnosis of IDD in NOD mice was characterized by thirst and weight loss, and persistent hyperglycemia of more than 240 mg/dl. For health maintenance, all diabetics received daily insulin doses of protamine-zinc insulin (Eli Lilly, Indianapolis, Ind.) at 0.5 to 2.0 units daily.

BALB/c islets were isolated according to the method of Brundstedt (Brundstedt, J., Nielsen, J. H., Lernmark, A., and the Hagedorn Study Group: in *Methods in Diabetes Research*, J. Larner, S. L. Pohl, Ed. [John Wiley & Sons, New York, 1987]), and labeled with $^{35}S$ methionine. Islet cells were washed twice (4° C.) in supplemented RPMI 1640 (GIBCO, New York) medium (2.0% fetal calf serum, 100 units/ml penicillin, 100 µg/ml streptomycin), followed by one wash in buffer containing 20 mM Tris (pH 7.4), 150 mM NaCl, 1000 KIE/ml traysylol and 2 mM PMSF. Cells were then lysed in the above buffer containing 1% Nonidet P-40 (NP-40) (v/v). Insoluble material was removed by ultracentrifugation (100,000×g, 30 min). The lysate was incubated with normal mouse serum (Balb/c) (10 µl per 100 µl supernatant, 1 h, 4° C.) followed by adsorption to an excess of protein A Sepharose CL-4B. This incubation/adsorption procedure was repeated 3 times.

Aliquots (100 µl) of unbound (pre-cleared) lysate were incubated with 25 µl of either NOD or control sera for 18 h (4° C.). To each assay tube, 100 µl of pre-swollen protein A Sepharose CL-4B were added, and the reaction mixture was incubated for 45 min (4° C.). The protein A Sepharose CL-4B was then washed five times by centrifugation (200× g, 10 sec) in 0.5% NP-40 buffer and once in cold water (200×g, 30 sec). Bound immune complexes were denatured by boiling for 5 min in sample buffer containing 80 mM Tris (pH 6.8), 3.0% (w/v) sodium dodecyl sulfate (SDS), 15% sucrose, 0.001 bromphenyl blue and (5.0% v/v) β-mercaptoethanol. The Sepharose beads were removed by centrifugation (200×g, 1 min) and the supernatant electrophoresed through SDS 12% polyacrylamide separating gels, followed by coomassie staining and autoradiography.

The initial studies were to learn whether 64KA occurred in NOD mice. Sera were obtained from 8 female NOD mice with newly diagnosed IDD (mean age at onset: 104.5±13.5 days; range, 93 to 134 days) and 11 healthy control mice (2 male and 9 female, mean age: 97.7±30.4 days, range 50 to 120 days) of the BALB/c (n=5), C57BL/6 (n=4), and C3H/HeJ (n=2) strains.

The 64KA was detected in 87% of NOD at the onset of their diabetes, but in none of the non-diabetes prone control strains (P<0.001). The presence of the 64K autoantibody in a high percentage of NOD mice with newly diagnosed IDD in conjunction with the absence of 64KA in age-matched non diabetes prone control mice, argues that the 64KA is specific for IDD and its prodromal state. The presence of 64KA was also one of the initial events detectable, being generally present even at or before weaning at the very earliest age that insulitis could be identified.

EXAMPLE 4

64KA as a Predictor of IDD in NOD Mice

In order to learn about the natural history of 64K autoantibodies with respect to IDD, serum samples obtained from 5 mice at weaning (2 male and 3 female; age 23–25 days) were analyzed and their pancreases examined histologically for insulitis. Insulitis was defined as an unequivocal intraislet infiltrate of lymphocytes on haematoxylon and eosin stained pancreatic sections containing 5 or more islets. The 64KA were already present in 80% (4/5) of these mice. Concomitantly, early insulitis was also present in 3 of the 4 mice whose pancreatic histologies were analyzed. In contrast, 2 animals (both male) studied at ≧190 days of age who had never developed IDD, had no 64KA, albeit both had insulitis.

EXAMPLE 5

64KA in BB Rats

In studies of IDD seen in BB rats (n=8), autoantibodies to the 64K protein appear early in the natural history of the disease and show considerable specificity (absence in 6 Lewis rat controls) as markers for IDD. The finding of 64KA in humans, NOD mice, and BB rats suggests that autoimmunity to the $M_r$ 64,000 islet cell protein may be of considerable pathogenic importance and that the 64K protein may have a vital physiological function in normal β-cells.

EXAMPLE 6

Biochemical Characterization of 64K Antigen

With respect to biochemical characterization, higher resolution of 64K protein gels suggest that it may consist of a doublet differing by approximately 0.5 kilodalton between the two components (63,500 and 64,000 $M_r$). The 64K component migrates to the $M_r$ 64,000 range under reduced conditions, and may be found as a dimer (approx. 130K) under non-reducing conditions. The 64K protein displays charge heterogeneity in that it has an isolectric point of 6.4 to 6.7. The 64K component most likely represents an integral islet cell membrane protein, due to its hydrophobic nature observed in immunoprecipitation of detergent phase extracts. As used in this patent application, the term "64K antigen" refers to the compound, compounds, or complex which behaves on a gel in the manner described herein. The 64K antigen can also be identified by its immunologic reactivity with anti-GAD antibodies as described below.

We have also observed that immunoprecipitation of detergent extracted from human islet cell proteins with sera from persons with IDD often results in the identification of a $M_r$ 67,000 protein. We analyzed for autoantibodies to this 67,000 $M_r$ antigen in a population of United States school children and relatives of a proband with IDD. The autoantibodies to the 67,000 $M_r$ protein were observed in 60% (12/20) newly diagnosed IDD patients, and were observed in only 1 of 18 controls (5%, P<0.001). In this IDD population, the autoantibodies to the 67,000 $M_r$ were often (73%, 11/15) observed in persons positive for 64KA, with only one 67,000 $M_r$ autoantibody positive but 64KA lacking patient. The autoantibodies to the 67,000 $M_r$ protein were present in only 1 of 34 (3%) non-diabetic first degree relatives who lacked both 64KA, islet cell cytoplasmic autoantibodies, and insulin autoantibodies. Analysis of commassie stained SDS-PAGE gels revealed that the presence of autoantibodies to the 67,000 $M_r$ protein was often associated with an intense staining protein of 70,000 $M_r$. Gas phase amino acid sequencing of this 70,000 $M_r$ protein revealed it to be an immunoglobulin V-III region chain, thereby pointing toward an IgM class of antibody. Therefore, immunity to the 67,000 $M_r$ antigen may be increased in but not restricted to IgM class antibodies. Also, whereas we have clearly shown that almost all 67,000 $M_r$ autoantibody positive patients also contain 64KA, the observation of 67,000 $M_r$ autoantibody positive but 64KA negative persons was rare. Therefore, we believe there may exist antigenic cross-reactivity between the 64,000 and 67,000 $M_r$ islet cell antigens, and that the autoantibodies to these proteins can identify these immunologically cross-reactive epitopes.

As used in this application, "immunological equivalents of 64K antigen" refers to peptides which react with the 64KA. The terms "64KA or 64K autoantibody" refer to the compound or compounds which react with the 64K antigen.

Because the 64,000 $M_r$ protein shows an amphiphilic nature, we performed experiments to observe if the 64K protein was essentially restricted to the cellular plasma membrane, and if so, was there also evidence for surface expression of this protein in normal islet cells.

Our biochemical characterization studies have shown no evidence for glycosylation of the 64K protein, a characteristic common to surface expressed proteins. A series of broad spectrum enzymes that would detect the common forms of protein carbohydrate glycosylation were used. This analysis used the enzymes N-GLYCANASE™ (for N-linked carbohydrates), treatment for O-linked carbohydrates, neuraminidase (for sialic acid groups), and β-endogalactosidase (for galactose groups). If one of the carbohydrate groups was present on the 64K protein, the enzyme would cleave that carbohydrate, and upon subsequent SDS-page analysis the mobility of the 64K protein would increase, and show a protein of decreased molecular weight. There were no detectable differences in the mobility of the 64K protein in SDS-page gels after treatment of the protein with this particular series of enzymes. Also, we have extensively analyzed the 64K protein for the presence of glycosylation using a series of 19 broad and narrow spectrum charbohydrate binding lectins. However, none of these lectins bound to the 64K proteins. Thus, it appears that there is no glycosylation of the 64K protein.

Finally, it has been previously shown (Colman et al., [1987] Diabetes 36:1432–1440) using a standard technique of radioactively labeling cell surface proteins with $^{125}$I, that no 64K protein could be immunoprecipitated from surface labeled islet cells with sera from diabetic patients. It was proposed in that work that the evidence for surface expression was therefore absent. However, that common technique labeled tyrosines (a relatively rare amino acid that may not be present at the extracellular portion of the protein), and was stringent in nature. Thus, it could be stringent enough to destroy the antigenic binding site of the 64K protein so that the antibody could no longer bind to the protein. However, we used a newly described technique (Thompson, J. et al. [1987] Biochemistry 26:743–750), that was much less stringent in chemical nature, one which radiolabeled lysines (an amino acid much more common that tyrosines) or $NH_2$-terminal amino acids, and one that was shown to label cell surface proteins with a much higher specific activity than the method used in the Colman et al. paper. Cell surface amino groups were derivatized with $^{125}$I (hydroxyphenyl) propionyl groups via $^{125}$I sulfosuccinimidyl (hydroxyphenyl) propionate. However, even with these assay improvements, no 64K protein could be immunoprecipitated from intact cell surface labeled human islet cells.

In order to confirm that the 64K protein was indeed present within the plasma membrane, we made crude membrane preparations of islet cells, and using the reagent Triton X-114, immunoprecipitated the 64K protein using sera from patients with IDD. Next, we developed an improved method for the detection of autoantibodies to 64K protein. The method used no detergent, and it gives a result that is easier to interpret and more rapid to perform. The method involves making crude membrane preparations of $^{35}$S methionine labeled islet cells, followed by trypsinization for 60 minutes at 4° C. (2 mg/ml 50 mM Tris buffer, pH 7.4). The material is then centrifuged, followed by our standard immunoprecipitation technique. Following gel electrophoresis and autoradiography, a 40K band can be observed with immunoprecipitations from diabetic sera and not in controls. As we have also shown that isolated 64K protein treated with trypsin also reveals a 40K protein, this 40K band that is immunoprecipitated directly from trypsin treated islets most likely represents the same protein. Not only is the assay for the 40K protein an improvement for simpler detection of 64KA, it also yields a product that is much more amenable to gas phase sequence analysis using imobilon membrane. The reason for this improvement is that the 40K fragment is most likely devoid of a major hydrophobic region that has caused difficulties in our determination of N-terminal amino acid sequence of 64K protein bound to IMMOBILON™ using the Applied Biosystems gas phase sequencer. It has been established that proteins with strong hydrophobic regions solubilize with solvents used in the gas phase sequencer, and therefore represent a major technical hurdle to direct sequencing of this protein. It is also much easier to visualize the 40K protein than the 64K protein in silver staining of the SDS page gels; due to lower background staining in the 40,000 $M_r$ range than in the 64,000 $M_r$ range.

Gas phase amino acid sequencing of either the intact 64K protein, or the trypsin cleavage fragment of 40K, has revealed $NH_2$-terminal blockage. This information, taken together with that of the soluble nature of the 40K fragment, would suggest that the 64K protein is anchored in the β-cell plasma membrane near its COOH terminus. Specifically, we would predict a series of three to four highly charged amino acids followed by a string of hydrophobic amino acids to be present in the 230 amino acids nearest the COOH terminus.

EXAMPLE 7

Phosphorylation of the 64K Protein

Many key regulatory proteins exist in cells as either a phosphorylated or dephosphorylated form, their steady-state levels of phosphorylation reflect the relative activities of the protein kinases and protein phosphatases that catalyze the interconversion process. Phosphorylation of serine, threonine, or occasionally tyrosine residues triggers a small conformational change in these proteins that alter their biochemical properties and biological properties. Hormones and other extracellular signals transmit information to the interior of the cell by activating transmembrane signalling systems that control the production of a relatively small number of chemical mediators termed "second messengers". These substances in turn regulate the activities of protein kinases and phophatases, and so alter the phosphorylation states of many intracellular proteins.

Although the full extent of the protein kinases within the human islet remains to be identified, we have applied the in vitro kinase assay using sera and islet cell proteins as an approach to identify any protein kinases which many have a role in the autoimmune destruction that results in IDD.

Two groups of individuals were selected for the in vitro kinase assay studies. There were 7 new onset IDD patients diagnosed according to the established National Diabetes Data Group (NDDG) criteria (National Diabetes Data Group. *Diabetes*, 1979; 28:1039–57), that had been referred to the University of Florida, Diabetes Clinics. We also studied 8 non-diabetic controls without any known family history of autoimmune disease. Human pancreatic islets isolated from cadaveric pancreases, were of 91.2±2.3% purity, and had insulin content of 0.4±0.1 mU insulin per islet. Following 48 hours of in vitro culture including the exclusive use of normal human serum, the islet cells were immunoprecipitated as follows: Immune complexes were prepared with sera from either patients with IDD or controls that were incubated with islet cell detergent extracts, followed by incubation with gamma $^{32}$P-ATP, and the products phosphorylated in vitro were analyzed on SDS-PAGE gels. Islet cells (1000/test sera) were lysed (3 h, 4° C.) in 50 mM Tris buffer (2% Triton X-114, Aprotinin, PMSF, NaF). The detergent lysates were incubated with normal human serum (100 μl/1000 islets), followed by adsorption to an excess of protein A Sepharose CL-4B (Pharmacia). Aliquots containing unbound (pre-cleared) lysate were incubated with either IDD or control sera (25 μl, 18 h, 4° C.). Following incubation of the immunoglobulins with the protein A Sepharose CL-4B (2 h, 4° C.), the complexes were then washed 3 times with 50 mM Tris-HCl (pH 7.4) with 0.1% SDS, 1.0% Triton X-114, and 2 mM EDTA, and two times with 50 mM Tris-HCl (pH 7.4). Kinase reactions were initiated by adding 10 μl of 50 mM HEPES buffer (pH 7.4) containing 10 mM MnCl$_2$, 10 mM MgCl$_2$, 1% Triton X-114, and 20 μCi of adenosine (gamma-$^{32}$P) 5' triphosphate (Amersham, >5000 Ci/mmol). The precipitates were suspended and incubated for 10 minutes at 30°. Reactions were terminated by the addition of electrophoresis sample buffer and heated to 95° C. for 4 minutes. The $^{32}$P labeled products were separated by discontinuous SDS 15% polyacrylamide separating gels, followed by autoradiography from 6 to 72 hours with intensifying screens (Kodak, X-omat AR5). The IDD patients sera specifically immunoprecipitated an M$_r$ 64,000 protein, which was not observed with the control sera.

More than 65 protein kinases have been identified to date (Hanks et al. [1988] Science 241:42–52), and can be classified according to the amino acid(s) phosphorylated. Identification of phosphorylated serine, threonine, and tyrosine residues can be accomplished by isolation and analysis of the $^{32}$P labeled protein from SDS-PAGE gels. IMMOBILON™, a membrane of polyvinylidene difluoride to which SDS-PAGE fractionated proteins can be transferred electrophoretically, was used as a matrix for the analysis of the phosphoamino acid content of the phosphoproteins. $^{32}$P labeled M$_r$ 64,000 protein bound to IMMOBILON™ was acid hydrolysed and the released phosphoamino acids and phosphopeptides were analyses by two-dimensional electrophoresis. The membranes were either subjected to autoradiography directly, or to base hydrolysis (1.0N HCl, 2H, 55° C.) prior to autoradiography. Following alignment of the autoradiograph with the immobilon membrane, the M$_r$ 64,000 containing protein was isolated (cut) from the IMMOBILON™ membrane, and subjected to acid hydrolysis (5.7N HCl, 1 h, 110° C.). The hydrolysis products were analyzed by two-dimensional paper electrophoresis after suspension in buffer containing authentic phosphotyrosine (Y), phosphoserine (S), and phosphothreonine (T) standards. Separation was performed for 4 hours at 900 volts from left (cathode) to right (anode) in acetic acid-formic acid-water (15:5:80, pH 1.9). The paper was then rotated 90° for electrophoresis in the second dimension from the bottom (cathode) to top (anode) in acetic acid-pyridine-water (5:0.5:94.5, pH 3.5) for 1.5 hours at 900 volts. The dried paper was analyzed by a BETAGEN™ analyzer, and the radioactive spots were aligned with the phosphoamino acid standards visualized by ninhydrin staining (Cooper, J. et al. [1983] Methods Enzymol. 99:387–402). Using this technique, we identified the 64,000 M$_r$ protein to have serine phosphorylation specificity; hence, it was phosphorylated through the action of a serine kinase. Because the detection of $^{32}$P labeled phosphotyrosine containing proteins have been shown (Kamps, M. et al. [1989] Analytical Biochem. 176:22–27) to be substantially improved by incubation of the IMMOBILON™ with base prior to acid hydrolysis, parallel 2-dimensional phosphoamino acid studies using this technique were also performed. However, the base hydrolysis technique removed the $^{32}$P signal observed in phosphoamino acid analysis of the M$_r$ 64,000 protein. This observation is again indicative of a serine-linase specificity, and not a tyrosine specificity.

Further experimentation was performed in order to confirm the serine amino acid specificity for the phosphorylation reaction. Because of the availability of phosphotyrosine specific antisera (Boehringer Manheim, 1G2), western blots were performed (Towbin, H. et al. [1979] Proc. Natl. Acad. Sci. USA 76(9):4350–4354) using M$_r$ 64,000 protein transferred from SDS-Page gels to IMMOBILON™ membranes. Although a positive reaction was observed between the anti-phosphotyrosine antisera and a positive control phosphotyrosine, no reaction was observed between the M$_r$ 64,000 protein and the anti-phosphotyrosine antibody.

Finally, in order to analyze if the identity of the M$_r$ 64,000 protein detected by the in vitro kinase reaction was identical to that observed with immunoprecipitates of metabolically labeled islet cells, tryptic peptide mapping experiments were performed. Treatment of the $^{35}$S methionine labeled islet cell M$_r$ 64,000 protein immunoprecipitated with IDD sera showed a similar tryptic peptide mapping as that of the in vitro phosphorylated M$_r$ 64,000 protein.

Specifically, the 64,000 M$_r$ and 125,000 M$_r$ proteins were excised from SDS-PAGE gels, and the proteins were treated with 1 mg/ml of trypsin (3–30 minutes, 4° C.). The resulting proteins were re-run on SDS-PAGE gels. The 125,000 M$_r$ protein was not affected by this treatment. However, the 64,000 M$_r$ protein increased in mobility to the 40,000 M$_r$ range. Thus, this 64,000 $^{32}$P labeled islet cell protein shows the same M$_r$ (40,000) when treated with trypsin, as we have observed with the M$_r$ 64,000 $^{35}$S methionine labeled islet cell protein.

EXAMPLE 8

Further Biochemical Identification of the 64K Autoantigen

We have established that the 64K autoantigen shows homology with glutamic acid decarboxylase (GAD) and is immunoreactive to anti-GAD antibodies. The GAD enzyme is localized to the brain and pancreatic β cells. The biochemical characterization of GAD in the literature has been limited to its role in the formation of gamma aminobutyric acid (GABA), which is the major inhibitory neurotransmitter in the mammalian brain. This GAD sequence which was published by Kobayashi et al. (Kobayashi, Y., D. L. Kaufman, and A. J. Tobin. [1987] "Glutamic acid decarboxylase cDNA: Nucleotide sequence encoding an enzymatically active fusion protein," J. Neuroscience 7(9) :2768–2772) is reproduced here in FIG. 1.

Antigenic cross-reactivity between GAD and the 64K protein has been confirmed. A series of immunoprecipitations confirmed competition for binding to the 64K protein using the autoantibodies against the 64K protein and monoclonal antibodies directed toward GAD. Monoclonal antibodies which react with GAD proteins are readily available to those skilled in the art from, for example, the American Type Culture Collection (ATCC) at 12301 Parklawn Drive, Rockville, Md. 20852. The monoclonal antisera GAD-1 (ATCC HB184) is specific for binding to GAD.

For these studies, human islet cells were metabolically labeled with $^{35}S$ methionine and detergent phase separated as previously described. Next, the islet cell extract was divided into two samples of identical volume. Each sample was precleared twice with either control (64K autoantibody lacking) or IDD (64K autoantibody containing) sera. The preclearing step with IDD sera removes, or markedly decreases, the quantity of the 64K protein from the islet cell protein preparation whereas preclearance with control sera would not markedly affect the 64K protein quantity. Both the precleared samples (control and IDD) were then individually immunoprecipitated with monoclonal antibodies toward GAD. The results showed that preclearance with control (64K autoantibody negative) sera had no effect on the ability of monoclonal anti-GAD antibody to immunoprecipitate the 64K protein of islet cells. However, the use of 64K autoantibody-containing IDD sera as a preclearance agent markedly reduced the ability of the monoclonal anti-GAD antibody to immunoprecipitate the 64K protein of islet cells. This demonstrates the antigenic cross reactivity between the 64K autoantigen and GAD.

Sera from 65 individuals, including 15 new onset IDD patients, and sera from those sample individuals obtained 2–3 years after IDD onset; 10 individuals with IDD from 5–10 years duration, 20 control individuals; and 5 individuals at high risk for IDD were tested for anti-GAD activity. Immunity in the form of autoantibodies toward GAD was clearly associated with IDD.

As described above in Example 6, immunoprecipitation of islet cells with IDD sera sometimes not only results in the identification of the 64K protein, but some individuals also immunoprecipitate a protein of 67,000 $M_r$. This observation was especially noted when the detergent phase preparation did not result in a clean separation between the aqueous (primarily cytosolic) and detergent phase (membrane associated) proteins. Thus, the 64K protein can be found within islet cells in two forms; a 67,000 $M_r$ soluble (cytosolic) form, as well as a 64,000 $M_r$ hydrophobic (membrane) form. The major autoantigen in IDD is that of the 64,000 $M_r$ form, but autoimmunity to the 67,000 form is also present.

Gas phase amino acid sequencing of the 64K autoantigen which was isolated from $^{35}S$-labeled human islet cells revealed homology between the 64K protein and the GAD sequence shown in FIG. 1. This homology was discovered as described below:

The 64K autoantigen was isolated from $^{35}S$-labeled human islet cell as previously described. After SDS-PAGE, the protein from the gels was transferred to IMOBILON-P™ membrane, and visualized by autoradiography. The 64K bands were localized, excised, and treated with cyanogen bromide which cleaves the peptide chain at methionine residues. The resulting peptide fragments were eluted from the PVDF membrane, and re-run on SDS-PAGE, followed by transfer to IMOBILON-P™. The bands were visualized by autoradiography and a fragment at $M_r$ 33,000 was excised and subjected to gas phase peptide sequencing. For example, the following sequence profile was obtained:

MET-ILE-PRO-GLU-VAL-LYS

We identified a high degree of similarity between the 64K amino acid sequence and GAD on two levels. First, as mentioned previously, the treatment of our 64K protein with cyanogen bromide resulted in a peptide fragment of 33,000 $M_r$. One would anticipate the fragment would consist of approximately 300 codons (900 nucleotides). Examination of the GAD sequence shown in FIG. 1 reveals an open reading frame of 625 codons in the entire protein, and 1875 nucleotides. Nucleotide positions 916 to 933 of that sequence code for the following amino acids:

PHE-PHE-PRO-GLU-VAL-LYS

Therefore, the 64K peptide sequence showed a high similarity in amino acid sequence to a GAD sequence. Moreover, this GAD peptide sequence was located in the region of the protein where we would expect to observe a 33,000 $M_r$ peptide upon cleavage with cyanogen bromide if a PHE to MET amino acid subsitution were made at that position. Second, the nucleotide differences between a deduced amino acid sequence (MET-PHE-PRO-GLU-VAL-LYS) and the nucleotide sequence 916 to 933 would involve only a minor nucleotide substitution. In fact, it is likely that methionine rather than phenylalanine is in the first position of the 64K sequence of this protein because the peptide was cleaved with cyanogen bromide which shows a specificity for methionine. We, therefore, have used the above sequence information to construct a probe to identify the gene coding for human pancreatic cell 64K protein from our DNA library.

A mixed oligonucleotide of the following sequence has been synthesized:

```
AAA TTTCCA GAA GTA AAA
     C  G    G   G   G
              C       C
              T       T
```

This synthetic oligonucleotide was radiolabeled using T4 poly nucleotide kinase and gamma $^{32}P$-ATP and used as a probe of the human islet cDNA library. Approximately 120,000 clones were screened and three positive plaques were detected.

The plaques that contained inserted DNA sequences can now be grown further and single-stranded M13 DNA prepared for them. The nucleotide sequence of the inserted DNA can then be determined using the dideoxynucleotide chain terminator method where a synthetic oligonucleotide serves as a primer for second strand DNA synthesis by a DNA polymerase (i.e., DNA polymerase I—Klenow fragment, or T7 DNA polymerase [SEQUENASE™]).

The information derived from the DNA sequence of the positive cDNA clone will be used for several purposes. The cloned sequence will be introduced into an appropriate prokaryotic expression vector for the production of large amounts of recombinant protein. This product will be used for the development of assays (eg ELISA, RIA, etc) for the determination of levels of anti-64K antibody in pre-diabetic patients or for diagnosing pre-diabetic individuals. In the event that the prokaryotic recombinant protein is not functional in this assay, an appropriate eukaryotic expression vector will be employed for the production of native 64K in eukaryotic cells. This is to overcome the possibility that bacteria cannot process the 64K precursor properly so that it is recognized by the autoantibodies.

Considerable interest has recently focused on antigenic determinants on proteins that are recognized by the effectors of the immune system (Benjamin, D., J. Berzofsky, I. East, F. Gurd, C. Hannum, S. Leach [1984] "Protein antigenic structures recognized by T cells: the antigenic structure of proteins; a reappraisal," Ann. Rev. Immunol. 2:67–101). A great deal of knowledge is available on T-cell and antibody binding epitopes based upon algorithms predicting T and β-cell epitopes (De Lisi, S., and J. A. Berzofsky [1985] "T cell antigenic sites tend to be amphipathic structures," Proc. Natl. Acad. Sci. 82:7048–7052; Hopp, T. P., and K. R. Woods, [1981] "Prediction of protein antigenic determinants from amino acid sequences," Proc. Natl. Acad. Sci. 78:3824–3828). In addition, experimental studies on model protein antigens such as cytochrome C have allowed the precise localization of T and B cell sites and the characterization of the critical amino acid residues important for recognition (Milich, D. R. [1989] "Synthetic T and B cell recognition sites: implications for vaccine development," In: Dixon, F. J. ed. *Advances in Immunology.* Vol. 45 Academic Press, London 1989; 195–282). However, in human organ-specific autoimmune disease, the lack of knowledge on the nature of the autoantigen and its availability has limited epitope studies (Mackay, I. R. and M. E. Gershwin. [1989] "Molecular basis of mitochondrial autoreactivity in primary billiary cirrhosis," Immunol. Today 10:315–318). In organ-specific autoimmune disease, the knowledge of the nature of the autoantigenic regions recognized by T cells and autoantibodies will allow the design of antagonists and immuno-modulatory compounds to combat tissue damage disease.

For these studies, cloned cDNA templates of GAD will be used in conjunction with the DNA amplification techniques to express selected segments of the 64K antigen as recombinant protein in *E. coli*. Multiple, overlapping, different recombinant fragments averaging 80 amino acid residues and larger fragments which will encompass the entire extracellular region of the molecule will be produced, and autoantibody-binding sites will be analyzed by immune precipitation of the expressed, bacterial products that had been grown in the presence of radioisotopically labeled precursors. The use of these will then allow studies to progress on epitope mapping of the precise antigenic amino acid sequences of the GAD molecule with the use of synthetic peptides. This principle has been applied previously to the epitope mapping of the autoantigenic epitope on recombinant thyroid peroxidase fragments.

With the knowledge of the precise autoantigenic epitope, synthetic peptides corresponding to this sequence will be used to produce a vaccine for the prevention of IDD similar to that proposed for vaccine development in general (Milich, [1989] supra.). These synthetic peptides will also be employed for the development of diagnostic reagents to be used in similar assays developed with the recombinant protein described above.

EXAMPLE 9

Collection of Biological Fluid for Detection of 64K Autoantibodies

A volume of greater than 500 microliters of whole blood is collected from the individual to be tested for 64KA autoantibodies. The blood is drawn into a glass vacutainer tube directly, or into a syringe followed by transfer into a glass vacutainer tube. In order to obtain sera (blood devoid of clotting factors), the common vacutainer tubes used are termed a red top tube (devoid of sodium heparin), or a serum separator (STS) tube. If a common red top tube is used, the tube is allowed to clot (a period of greater than 10 minutes), and the clot removed. At this period of time, either sample tube may be centrifuged for 5 minutes at 1000 rpm at room temperature. The serum within the sample is removed and placed into a plastic storage vial and sealed tightly. The sample can be frozen at −20° until 64K autoantibody analysis.

EXAMPLE 10

Preparation of 64K Antigen for Use in Testing Biological Fluids

Before a sample can be tested for 64K autoantibodies, human islet cell preparations must be isolated and metabolically labeled to provide a source of 64K antigen. Human islet cell preparations can be isolated from cadaveric human pancreatic donors as outlined in detail according to the method of Ricordi et al. (Ricordi, C., Lacy, P. E., Finke, E. H., Olack, B. J., and Scharp, D. W. [1988] "Automated method for isolation of human pancreatic islets," Diabetes 37:413–420). Islet cells can be stored in T-150 plastic tissue culture flasks at a concentration of 6,000 islets/T-150 flask in 50 milliliters of CMRL media.

Before testing, the CMRL media is removed and discarded. To each flask, 50 milliliters of RPMI 1640 media (supplemented with 16 mM glucose, 100 µU/milliliter Penicillin, 100 µG/milliliter Streptomycin, and 2% v/v normal human serum) are added to each flask, and allowed to incubate overnight in culture at 37° C. in an atmosphere of 95% air/5% $CO_2$. The islets are collected into centrifuge tubes at a concentration of 50 milliliters of media per tube.

The tubes are capped and centrifuged for 3 minutes at 1000 rpm at room temperature. The supernatant is removed and discarded. A small amount (approximately 4 milliliters) of RPMI labeling media (supplemented with 16 mM glucose, 20 mM HEPES, 2% normal human serum, and free of the amino acid methionine) is added to each tube with gentle mixing for approximately 30 seconds per tube. All islet cells are then collected into one 50 milliliter polypropylene centrifuge tube and centrifuged at 1000 rpm for 5 minutes. The supernatant is removed and discarded. The islet cells are then resuspended in RPMI labeling media (1000 islet/milliliter media), and transferred to a 100 mm plastic tissue culture petri dish. The islets are incubated for 15 minutes at 37° C. (95% air/5% $CO_2$), after which time $^{35}S$ methionine is added to the media at a concentration of 0.5 mCi/1×10⁴ cells. The islet cells are once again incubated for 5 hours at 37° C. (95% air/5% $CO_2$). The media within the petri dishes is aspirated without disrupting (or collecting) the islet cells, and the media disposed of.

To the cells is then added an equivalent volume of RPMI 1640 media at a concentration of 1000 islets/ml and incubation at 37° C. (95% air/5% C02) for 30 minutes. The islet cells and their media are collected into 15 ml conical polypropylene centrifuge tubes. The tubes are filled to the 15 ml marking with buffer containing 20 mM Tris (pH 7.4), 150 mM NaCl, 1000 KIE/ml aprotinin and 2 mM phenylmethyl sulfonyl fluoride, capped, centrifuged (1000 rpm, 5 minutes), and the supernatant discarded. The tube containing the pellet can then be frozen (−80° C.).

EXAMPLE 11

Detergent Extraction of 64K Antigen and Testing of Biological Fluid for 64K Autoantibodies In order to perform immunoprecipitation of the 64K antigen using test sera, the islet cells are slowly thawed in their tube on ice. Once thawed, a detergent extraction buffer (20 mM Tris (pH 7.4), 150 mM NaCl, 1000 KIE/ml aprotinin and 2 mM phenylmethyl sulfonyl fluoride, and 2% TRITON™ X-114) is added to the tube, and the islets lysed for 3 hours on ice. In addition, the islets are sonicated within their tube for a total of 60 seconds (4 times at 15 second intervals with 1 minute rests on ice between each sonication) using a sonication probe inserted into the detergent extract. At 15 minute intervals, the islets are also mechanically disrupted.

The insoluble material is removed from the detergent extracted islets by pipetting equal volumes of the extract into centrifuge tubes, placing the balanced tubes into a Beckman type 50 rotor, and ultracentrifuging the tubes (100,000×g, 30 minutes, 4° C.). The supernatant is removed and placed into a new polypropylene tube. The pellet may be discarded. The islet cell lysate (supernatant) can then be separated into aqueous, sucrose, and detergent phases prior to immunoprecipitation studies.

The method for detergent phase extraction is followed directly from the methodology of Bordier (Bordier, C. [1981] "Phase separation of integral membrane proteins in TRITON™ X-114 solutions," *J. Biol. Chem.* 256:1604–07).

After extraction, the detergent phase of the islet cell lysate is then incubated in a capped 1.5 ml epindorf tube with normal human serum (10 µl of test sera per 100 µl of detergent phase supernatant, 1 hour, 4° C. [ice bath]), followed by adsorption to pre-swollen protein A Sepharose CL-4B (can be purchased from Pharmacia, Sweden). One-hundred µl of swollen protein A sepharose CL-4B is added to each 400 µl of test sera/detergent phase mix in a capped 15 ml conical centrifuge tube, and maintained at 4° C., on a shaking platform @ 300 rpm for 2 hours). At that time, the tube can be centrifuged for 1 minute at 1000 rpm, and the supernatant removed. The protein A sepharose pellet can be discarded. Aliquots (100 µl containing 5–10×10⁶ cpm) of unbound (pre-cleared) lysate (supernatant) is distributed into 1.5 ml epindorf centrifuge tube and incubated with 25 µl of the sera which is to be tested for the presence of 64K autoantibodies. The tubes are then capped and incubated at 4° C. (ice bath) for 18 hours.

To each assay tube, 100 µl of pre-swollen protein A Sepharose CL-4B is added, and the reaction mixture is incubated for 2 hours at 4° C. on a shaking platform @ 300 rpm. To the tubes is added 900 µl of 0.5% TRITON™ X-114 buffer in order to wash the protein A Sepharose CL-4B. The tubes are vortexed for 10 seconds each, followed by centrifugation for 10 seconds at 1000 rpm. The supernatant is discarded by aspiration, and the pellet left remaining in the tube. Another 900 µl of 0.5% TRITON™ wash buffer is added to the tube, and the wash procedure repeated 5 more times. One final wash step occurs with the exception that ice cold water wash is substituted for the 0.5% TRITON™ buffer.

At this point, the tubes should only contain a pellet composed of protein A Sepharose CL-4B and any immune complexes formed between antibodies and/or islet proteins. The bound immune complexes can be removed and denatured by boiling for 3 minutes in 100 µl of sample buffer containing 80 mM Tris (pH 6.8), 3.0% (w/v) sodium dodecyl sulfate (SDS), 15% sucrose, 0.001 bromphenyl blue and (5.0% v/v) β-mercaptoethanol in the same capped 1.5 ml epindorf tube. The Sepharose beads are then removed by centrifugation of the tubes (1000 rpm, 1 minute) and the supernatant carefully removed. Fifty µl of the sample is then electrophoresed through discontinuous SDS 10% polyacrylamide separating gels followed by Coomassie Brilliant Blue staining, according to the method of Laemmli [Laemmli, U.K 1970. Cleavage of structural proteins during the assembly of the head of bacteriophage T4. *Nature.* 227:680–85], followed by fluorography using the methods detailed in the commercial product Enhance (New England Nuclear).

Following electrophoresis, the gels are placed on filter paper, and dried for 2 hours at 60° C. in a electrophoresis gel dryer. Once dry, the gels are removed and placed on X ray film (Kodak XR OMAT) in film cassettes with intensifying screens, and placed for 3 weeks at −80° C. The films (termed fluororadiographs) are processed using standard X ray film photo processing. Test samples are rated as positive or negative after comparison with their respective positive and negative controls.

EXAMPLE 12

Methods of Detecting 64KA

In addition to the use of immunoprecipitation techniques outlined in Example 11, the subject invention can be practiced utilizing any procedures which facilitate detecting the presence of 64KA. For example, other immunological methods which can be used include enzyme linked immunosorbent assay (ELISA) and radioimmunoassay (RIA). The principles and experimental methods of these procedures are well known to those skilled in the art. The assays can be carried out rapidly and efficiently by the use of natural or recombinant proteins which bind with the 64KA. Both whole cell and cell lysate procedures are familiar to those working in this field and can be readily employed to detect the 64KA of the subject invention.

For example, as described in Example 8, the amino acid sequence shown in FIG. 1 can be analyzed to ascertain immunologically reactive epitopes. These epitopes would be amino acid sequences which would react immunologically with the 64KA. These sequences could then be produced recombinantly. For recombinant production, the DNA coding for the epitopes could be inserted into a vector which would then be used to transform an appropriate host cell which would then express the desired amino acid sequence. Although bacteria, insects, yeasts, and mammalian cells could all serve as appropriate hosts, if protein folding is an important factor in the reactivity of the epitope, then a eukaryotic cell would be a preferred host.

Purified protein or lysate of the cells producing the protein could be used for the assays.

Also, an alternative to using 64K antigen to detect 64KA would be to use antibodies generated to 64KA, otherwise known as an anti-64KA antibody. This antibody would immunoprecipitate with 64KA, and the detection could be carried out as described above.

EXAMPLE 13

Assay for Detecting 64K Autoantigen-Autoantibody in Immune Complexes

Patients who have IDD or who are in the process of developing the disease can be expected to have, within their sera, immune complexes which comprise the 64K autoantigen. These immune complexes typically consist of the 64K antoantigen surrounded by several immunoglobulins. Because individuals who do not have the disease, or who are not developing it, would not have these immune complexes, the detection of these complexes provides the basis for an assay for detecting this disease.

Initially, blood is drawn from patients to be tested for IDD or from controls. Sera can be obtained by spinning out the red blood cells from the blood sample. For patients with IDD, or those who are developing the disease, this sera can be expected to contain the immune complexes which comprise the 64K autoantigen. Next, a sample of the sera can be incubated with protein A Sepharose. The volume of sample incubated with the sera may be small, for example, 25 µl. Following incubation of the immunoglobulins with protein A Sepharose CL-4B (2 hours, 4° C.), the complexes can be then washed 3 times with 50 mM Tris-HCl (pH 7.4) with 0.1% SDS, 1.0% Triton X-114, and 2 mM EDTA, and two times with 50 mM Tris-HCl (pH 7.4). By washing the sepharose as described, extraneous sera protein are washed away, leaving only immunoglobulins which have bound to the protein A Sepharose. The radioactive phosphorylation of the 64K autoantigen can then be accomplished utilizing a kinase reaction. Kinase reactions can be initiated by adding 10 µl of 50 mM HEPES buffer (pH 7.4) containing 10 mM $MnCl_2$, 10 mM $MgCl_2$, 1% Triton X-114, and 20 µCi of adenosine (gamma-$^{32}$P) 5' triphosphate (Amersham, >5000 Ci/mmol). The precipitates can be suspended and incubated for 10 minutes at 30°. Reactions can then be terminated by the addition of electrophoresis sample buffer and heated to 95° C. for 4 minutes. The $^{32}$P labeled products can be separated by discontinuous SDS 15% polyacrylamide separating gels, followed by autoradiography from 6 to 72 hours with intensifying screens (Kodak, X-omat AR5). The IDD patients sera specifically immunoprecipitate an $M_r$ 64,000 protein, which is not observed with the control sera.

EXAMPLE 14

Treatment of IDD using Hybrid Proteins Vaccines

The specific event or agent which triggers the onset of diabetes has not been identified. A virus carrying an antigen similar to the 64K antigen may provoke both a normal immune response to the virus and also an abnormal, autoimmune A response to the 64K antigen through its molecular mimicry with the virus. The genetic susceptibility is thus expressed by an exaggerated or prolonged immune response to the environmental agent which initiates the disease process. It is also possible that the 64K protein may have a delayed expression in the development of islet cells in ontogeny, rendering it antigenic because tolerance to it would not have been developed in the early stages of life.

Regardless of the mechanism of disease initiation, β-cell destruction could proceed in at least two ways. The 64KA could bind to the initiating exogenous antigen and stimulate other compounds of the immune system to destroy the antibody bound β-cells. Or, T-lymphocytes could recognize the 64K antigen and destroy the cells directly. In either case it is possible, using the 64K protein, to interfere with the destructive process, thereby delaying or preventing IDD.

The novel therapy of the subject invention involves the injection into the bloodstream of a toxin bound to a purified form of the 64K antigen. The antigen-toxin complex would quickly reach the lymph nodes where it is taken up by immune cells that normally produce the 64KA. Also, the antigen-toxin complex would be bound by the T-lymphocytes that recognize the 64K antigens on β-cells. Thus, the specific immune cells involved in β-cell destruction are poisoned and inactivated, leaving non-destructive immune cells unharmed.

The hybrid protein could comprise, for example, a diphtheria toxin joined together with the 64K antigen. The construction of such a hybrid toxin could proceed, for example, according to the disclosure of U.S. Pat. No. 4,675,382 (Murphy, 1987) relating to hybrid proteins.

An alternative method would involve the creation of an altered virus (from the disease-initiating class of viruses) which lacked expression of the "64K-like" proteins but retained infectivity. This attenuated virus could be used to vaccinate those at high genetic risk for IDD, i.e., HLA homologous siblings or those who are in the early stages of IDD. Likely candidates for viruses which may mimic the 64K protein and, thus, initiate the disease process include the coxsackie, rubella, and EMC viruses. A vaccine composition can be made which comprises an attenuated virus wherein the un-attenuated virus is responsible for causing an immune response to an epitope shared with the 64K protein. In the attenuated form, vaccine virus would elicit an immune response to the virus, but not to the 64K protein.

EXAMPLE 15

Use of 64KA in Conjunction with Pancreas Transplantation

A preferred approach for treatment of a patient with IDD would be to transplant normal islets as replacements for the damaged or destroyed β-cells. Segmental and whole pancreas transplantations have been performed successfully in a number of patients with diabetes. However, permanent immunosuppressive therapy is always required to maintain the grafts and prevent rejection. Segmental or whole pancreas transplants under continuous immunosuppressive therapy have produced normal levels of blood glucose in some patients with diabetes. Pancreatic transplants are done late in the course of diabetes and will probably not reverse complications such as nephropathy and indeed may worsen retinopathy.

Importantly, successful pancreatic grafts between identical twins have been maintained without immunosuppressors; however, autoimmune islet cell destruction has occurred with recurrence of diabetes. Thus, even when the graft is not rejected, there is obligatory need for immunotherapies to prevent disease recurrence. The destruction (rejection) of transplanted islets may be due, at least in part, to the re-presentation of autoantigens responsible for the autoimmune destruction. There is no specific immunotherapy to prevent the autoimmune destruction (rejection of transplanted islets/pancreas) at present. In order to prevent the autoimmune destruction of either transplanted islet cells or pancreas, a specific immunotherapy using a hybrid toxin, as detailed in Example 11, can be used to prevent islet cell destruction. The combined use of the immunotherapies could make islet cell/pancreas transplantation a therapeutic tool for the treatment of IDD.

EXAMPLE 16

Kits for Assay of 64KA

A reagent kit can be provided which facilitates convenient analysis of serum samples using the novel procedures described here. Kits can be prepared which utilize recombinant or synthetically produced intact 64K protein(s) or immunoreactive peptides to serve as an antigen for the detection of 64KA. Alternatively, antibodies specifically developed to detect 64KA may also be useful. The principles and methods for ELISA and RIA technologies to detect antibodies are well-established.

As an example, for the ELISA assay, one such kit could comprise the following components:

1. 64K protein, peptide, or anti-64KA antibody;
2. Enzyme (e.g., peroxidase);

3. Conjugated animal anti-human immunoglobulin; and
4. Positive and negative controls.

The above kit could be modified to include 96 well plastic plates, calorimetric reagents, ELISA readers, blocking reagents, and wash buffers.

Also by way of example, for the RIA, one such kit could comprise the following components:

1. Radiolabeled 64K protein(s), peptide, or anti-64KA antibody;
2. Wash buffers;
3. Polyethylene glycol;
4. Goat or sheep antihuman precipitating (second) antibodies; and
5. Positive and negative controls.

Either of the above kits may be modified to include any appropriate laboratory supplies.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for reducing the severity of insulin dependent diabetes wherein said method comprises administering to an animal a composition comprising an isolated GAD polypeptide.

2. The method of claim 1 wherein said GAD polypeptide is produced recombinantly.

* * * * *

UNITED STATES PATENT AND TRADEMARK OFFICE
CERTIFICATE OF CORRECTION

PATENT NO. : 5,762,937

DATED : June 9, 1998

INVENTOR(S) : Mark A. Atkinson and Noel K. Maclaren

It is certified that error appears in the above-identified patent and that said Letters Patent is hereby corrected as shown below:

Column 1, line 17: "filed Dec. 12, 1988," should read --filed Dec. 13, 1988,--.

Column 7, line 48: "of RNA The" should read --of RNA. The--.

Column 18, line 15: "serine-linase" should read --serine-kinase--.

Column 25, lines 36-37: ""autoimmune A response" should read --autoimmune response--.

Column 27, line 4: "calorimetric reagents, " should read --colorimetric reagents,--.

Column 28, line 10: "an isolated GAD polypeptide." should read --an isolated and purified GAD polypeptide.--.

Signed and Sealed this

Twenty-ninth Day of December, 1998

BRUCE LEHMAN

*Attest:*

*Attesting Officer*     *Commissioner of Patents and Trademarks*